(12) United States Patent
Watzele et al.

(10) Patent No.: US 7,919,268 B2
(45) Date of Patent: Apr. 5, 2011

(54) REDUCING SAMPLE TURBIDITY IN MEASUREMENT OF ENZYMATIC ACTIVITY IN CELL LYSATES

(75) Inventors: Manfred Watzele, Weilheim (DE); Thomas Nikolaus, Munich (DE); Hans-Juergen Rode, Sandhausen (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 12/409,038

(22) Filed: Mar. 23, 2009

(65) Prior Publication Data

US 2009/0181417 A1    Jul. 16, 2009

Related U.S. Application Data

(63) Continuation of application No. 11/608,943, filed on Dec. 11, 2006, now abandoned.

(30) Foreign Application Priority Data

Dec. 12, 2005 (EP) .................................. 05027062

(51) Int. Cl.
    *C12Q 1/32* (2006.01)
(52) U.S. Cl. .......................................................... 435/26
(58) Field of Classification Search .................. 435/26
    See application file for complete search history.

(56) References Cited

U.S. PATENT DOCUMENTS

| | | | |
|---|---|---|---|
| 4,282,001 A | | 8/1981 | Klose et al. |
| 4,556,634 A | * | 12/1985 | Misaki et al. ................ 435/25 |
| 4,622,296 A | * | 11/1986 | Yamanishi et al. ........... 435/26 |
| 5,250,420 A | * | 10/1993 | Asano et al. ................. 435/26 |
| 5,501,959 A | | 3/1996 | Lancaster et al. |
| 5,589,327 A | | 12/1996 | Hilyard et al. |
| 6,465,208 B1 | | 10/2002 | Rogers |
| 2003/0203420 A1 | * | 10/2003 | Riss et al. ................... 435/26 |
| 2005/0186557 A1 | | 8/2005 | Riss et al. |

FOREIGN PATENT DOCUMENTS

| WO | 2003/089635 A1 | 10/2003 |
|---|---|---|
| WO | WO 03/089635 A1 * | 10/2003 |

OTHER PUBLICATIONS

Vihola H. et al. Cytotoxicity of Thermosensitive Polymers . . . Biomaterials 26:3055-3064, Jun. 2005.*
Corey, Michael J. et al., "A very sensitive coupled luminescent assay for cytotoxicity and complement-mediated lysis," J. Immun. Meth., 1997, pp. 43-51, vol. 207.
Decker, Thomas, and Lohmann-Matthes, Marie-Luise, "A quick and simple method for the quantification of lactate dehydrogenase release in measurements of cellular cytotoxicity and tumor necrosis factor (TNF) activity," J. Immun. Meth., 1988, pp. 61-69, vol. 15.
Kamiya, N. et al., "Effect of Using Co-Solvent in the Preparation of Surfactant-Coated Lipases on Catalytic Activity in Organic Media," Journal of Fermentation and Bioengineering, 1996, pp. 37-41, vol. 82.
Korzeniewski, Carol and Callewaert, Denis M., "An Enzyme-Release Assay for Natural Cytotoxicity," J. Immun. Meth., 1983, pp. 313-320, vol. 64.
Martin, Angela and Clynes, Martin, "Letter to the Editor: Acid Phosphatase: Endpoint for in Vitro Toxicity Tests," In Vitro Cell Dev. Biol., 1991, pp. 183-184, vol. 27A.
Masanet, J. et al., "Hepatic Toxicity of Paraquat in Primary Cultures of Rat Hepatocytes," Toxic in vitro, 1988, pp. 275-282, vol. 2.
Szekeres, Julia et al., "Measurement of Lymphocyte Cytotoxicity by Assessing Endogenous Alkaline Phosphatase Activity of the Target Cells," J. Immun. Meth., 1981, pp. 151-154, vol. 40.
Vihola, H. et al, "Cytotoxicity of thermosensitive polymers poly(N-isopropylacrylamide), ploly (N-vinylcaprolactam) and amphiphilically modified poly(N-vinylcaprolactam)," Biomaterials, 2005, pp. 3044-3064, vol. 26.
European Search Report issued Feb. 3, 2006 in European Application No. 05027062.8.

* cited by examiner

*Primary Examiner* — Ralph Gitomer

(57) ABSTRACT

Disclosed are methods and kits for measuring enzyme activity in which the turbidity of a sample caused by cell components is minimized by particular additives. The methods include the steps of providing a cell suspension or a cell lysate containing cell components, adding a chromogenic substrate at the start of the enzyme reaction, adding a first additional substance to stop the enzyme reaction, and making a colorimetric measurement, wherein a second additional substance which reduces the light scattering and/or absorption caused by the cells or the cell components is added during or after termination of the enzyme reaction. In particular, a method is disclosed wherein the enzyme is lactate dehydrogenase (LDH) and the first additional substance to stop the reaction is HCl.

2 Claims, 2 Drawing Sheets

1. Step:

2. Step:

REDUCING SAMPLE TURBIDITY IN MEASUREMENT OF ENZYMATIC ACTIVITY IN CELL LYSATES

RELATED APPLICATIONS

This application is a continuation of U.S. Ser. No. 11/608,943 filed Dec. 11, 2006, now abandoned, and claims priority to European application EP 05027062.8 filed Dec. 12, 2005.

FIELD OF THE INVENTION

The present invention originates from the field of calorimetric measurement of enzyme activities in cellular suspensions or lysates. In particular the present invention concerns a method for measuring enzyme activities in which the turbidity of the sample caused by cell components is minimized by adding suitable additives.

BACKGROUND

If one wants to examine the effect of reagents, active substances or other influences on an organism, these experiments are often carried out in cell culture in in vitro models. The various enzymatic activities of cells yield information on their condition and physiological properties.

Often attempts are made to detect the activation of genes by means of so-called reporter gene tests. In these tests the gene for a certain detection enzyme (=reporter gene) is placed behind a promoter whose activation one wishes to detect. Secreted enzymes such as for example the secretory alkaline phosphatase, the activity of which is then tested with the enzyme substrate 4-nitrophenyl phosphate, can also be used for this as reporter genes. This substrate is converted by this enzyme into the product 4-nitrophenol which absorbs light at a wavelength of 405 nm.

If one wishes to genetically modify cells, one has to firstly transport the appropriate plasmid DNA through the plasma membrane and then into the cell nucleus with the aid of suitable methods. The methods used for this such as lipofection must be optimized in each case for the relevant cell line. Plasmids containing reporter genes such as the secretory alkaline phosphatase are also frequently used in these cases in which the aim is to optimize the transfectability of different cells. The success of the transfection can then be checked on the basis of the measured enzyme activity.

Different methods are also very frequently used to measure the cytotoxic properties of a substance. A number of tests for determining cytotoxicity may be found in the literature.

Many of these tests are based on the property of cytotoxic substances to damage the cell membrane. Enzymes which can be detected in the cell culture supernatant by an enzymatic test are released from cells whose plasma membrane has been damaged. The amount of released enzymes is proportional to the number of damaged cells. Such enzyme release tests have been described for glutamate-oxaloacetate transaminase, for glutamate pyruvate transaminase, for arginosuccinate lyase and for alkaline and acid phosphatase (Masanet, J., Gomez-Lechon, M. J., and Castell, J. V., Toxic. in Vitro 2 (1988) 275-282; Martin, Angela and Clynes, Martin, In Vitro Cell Dev. Biol. 27A (1991) 183-184). The release of alkaline phosphatase from human embryonic fibroblasts caused by lymphocytes was for example tested in this manner (Szekeres, Julia, Pacsa, A. S, and Pejtsik, B., J. Immun. Meth. 40 (1981) 151-154). However, lactate dehydrogenase is used most frequently for enzyme release tests since the aforementioned enzymes are often difficult to determine due to their small amount in many cells. In contrast to other enzymes lactate dehydrogenase is a very stable cytoplasmic enzyme which is present in all cells. It is very rapidly released from cells with a damaged plasma membrane and can be easily detected in the culture supernatant (Decker, Thomas and Lohmann-Matthes, Marie-Luise, J. Immun. Meth. 15 (1988) 61-69; Korzeniewski, Carol and Callewaert, Denis M., J. Immun. Meth. 64 (1983) 313-320).

In this test $NAD^+$ is reduced in a first step to $NADH/H^+$ by the LDH-catalysed conversion of lactate to pyruvate. In the second step a second enzyme (=catalyst diaphorase) transfers the $H/H^+$ from $NADH/H^+$ to the tetrazolium salt INT (2-[4-iodophenyl]-3-[4-nitrophenyl]-5-phenyltetrazolium chloride) which is reduced in this process to the formazan (FIG. 1). The formazan dye is water-soluble and has a broad absorption maximum at 500 nm, while the substrate INT does not absorb at this wavelength (FIG. 2).

In other methods for measuring cytotoxicity fluorescent substrates such as resazurin are used instead of colorimetric enzyme substrates to measure LDH (Cytotox-One™ assay from the Promega Company, Madison, Wis.) or glucose-6-phosphate dehydrogenase (Vybrant Assay from the Molecular Probes Company from Eugene, Oreg.) in a similar reaction mixture. In other methods released glyceraldehyde-3-phosphate dehydrogenase is used to synthesize ATP by a coupled enzyme reaction. The ATP that is formed in this reaction is used in a bioluminescence reaction with luciferin and luciferase in which a measurable light signal is generated (Corey, Michael J., et al., J. Immun. Meth. 207 (1997) 43-51).

In addition to the tests for measuring a destroyed plasma membrane, the physiological activity and proliferation rate of cells is often also determined by means of their ability to reduce certain colour substrates. Colour substrates are used for this which change their colour when they are reduced in such a manner that only the product absorbs light of a certain wavelength which is then measured. Known reagents for this are for example tetrazolium salts such as MTT (3-(4,5-dimethylthiazol-2-yl)-2,5-diphenyltetrazolium bromide), XTT (sodium 3'-[(1-phenylamino-carbonyl)-3,4-tetrazolium]-bis (4-methoxy-6-nitro)-benzylsulfonic acid hydrate) and WST-1 which are offered by Roche Applied Science (Mannheim, Germany) under the names Cell Proliferation Kit I (MTT), Cell Proliferation Kit II (XTT) and Cell Proliferation Reagent WST-1.

In addition to the tetrazolium salts, the blue dye resazurin is also used which is converted on reduction into the red strongly fluorescent dye resorufin which can be measured calorimetrically as well as fluorimetrically (Lancaster et al., U.S. Pat. No. 5,501,959).

WO 2003/089635 describes a combination of reagents for determining released LDH with the substrates resazurin or MTS (3-(4,5-dimethylthiazol-2-yl)-5-(3-carboxymethoxyphenyl)-2-(4-sulphophenyl)-2H-tetrazolium, internal salt). The reduced form of MTS is measured colorimetrically and the reduced form of resazurin is measured colorimetrically or preferably fluorimetrically. In the case of this combination of reagents it is also suggested that a stop reagent should be added which stops the reaction. A soap or a detergent or a strong base such as NaOH is suggested as the stop reagent. A 3% SDS solution is recommended as the soap or detergent. A person skilled in the art is very familiar with the protein-denaturing properties of SDS where the reaction is stopped due to the denaturation of LDH. NaOH stops the reaction by changing the pH. However, only a very few known detergents or soaps result in a reaction stop as shown by the examples given below. The teaching in WO 2003/089635 would thus be to use such detergents or soaps which would result in a reaction stop i.e. which have protein-denaturing properties. Furthermore, with regard to the soaps or detergents stated in this patent no indication is given that they can be used to reduce light scattering or absorption caused by cells and thus to increase the sensitivity of calorimetric measurements.

In all methods in which an enzyme activity is detected calorimetrically in the presence of cells, the problem arises especially in the case of high cell counts that the light is scattered and absorbed by the cells in the entire wavelength range of visible light. Thus for example in the method described by Decker and Lohmann-Matthes for measuring released lactate dehydrogenase it is pointed out that in the case of high cell counts it is better to transfer the cell-free supernatants from the cell culture plate into new reaction vessels because of the observed high absorption of the cells and to measure the enzymatic activity in these reaction vessels. This procedure requires a centrifugation of the culture plates and a careful removal of the culture supernatant. These are additional working steps which make it more difficult to use the method for high throughput analysis for example with the aid of appropriate robots. In addition the cells may be damaged by the centrifugation or the removal of the supernatant thus releasing cytoplasmic enzymes which can interfere with the test result.

In the other methods in which a fluorimetric or a chemiluminescent measurement is carried out it is not possible to work with the widely used colorimetric measurement instruments especially for standard microtitre plates, the so-called ELISA readers, which considerably restricts the use of these substrates. In the case of chemiluminescent substrates the signal is often stable for only a relatively short period which requires a rapid measurement directly after the end of the test.

In the method published in WO 2003/089635 for determining released LDH using the substrates resozurin or MTS, these substrates are also described for colorimetric measurements. NaOH or SDS is claimed as a stop reagent. However, it must be noted that the colorimetric measurement of reduced resazurin only allows a low sensitivity. The use of NaOH or SDS with tetrazolium salts such as MTS is disadvantageous since NaOH leads to a precipitation of reduced tetrazolium salts (see example 2 of this application). Also SDS is not preferred since in this case tetrazolium salts are surprisingly bleached out relatively rapidly (see example 2 of this application).

SUMMARY OF THE INVENTION

Hence the present invention concerns a method for the colorimetric measurement of enzyme activities comprising the following steps:
  preparing a cell suspension or a cell lysate containing cell components
  adding a chromogenic substrate at the start of the enzyme reaction
  adding a first additional substance to stop the enzyme reaction
  calorimetric measurement
which is characterized according to the invention in that a second additional substance which reduces the light scattering and/or absorption caused by the cells or the cell components is added during or after termination of the enzyme reaction.

This can for example be achieved by means of the fact that the second additional substance is a substance which adjusts the refractive index of the suspension or of the lysates to that of the cells or cell components.

Alternatively this can be achieved by means of the fact that the second additional substance is a substance which, due to its molar concentration, removes water from the cells or cell components by osmotic pressure.

This can preferably also be achieved by means of the fact that the second additional substance dissolves the cell membrane. Such substances can for example be various types of detergents and also certain proteins or peptides.

In addition the present invention also encompasses kits for the calorimetric measurement of enzyme reactions in cell suspensions or cell lysates containing cell components comprising
  a chromogenic substrate
  a first substance to stop the enzyme reaction
  a second substance which, when added, reduces the light scattering and/or absorption caused by the cells or the cell components.

The second substance can for example according to the invention adjust the refractive index of the suspension or of the cell lysate to that of the cells or cell components.

Alternatively a second additional substance can, due to its molar concentration, remove water from the cells or cell components by osmotic pressure.

The second additional substance can preferably dissolve cell membranes.

DETAILED DESCRIPTION OF THE INVENTION

Figure 1:
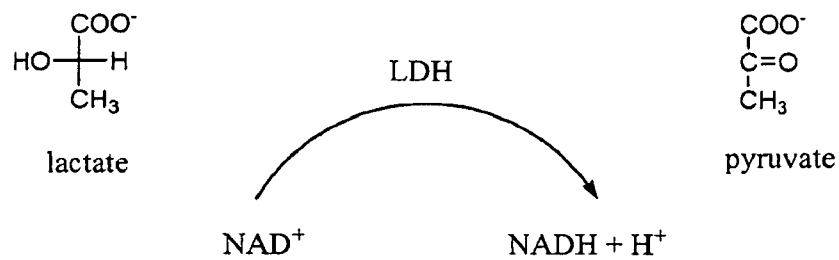
FIG. 1: In the first step lactate dehydrogenase (LDH) released into the medium reduces $NAD^+$ to $NADH+H^+$ by oxidizing lactate to pyruvate. In the second enzymatic reaction 2H from $NADH+H^+$ are transferred to the tetrazolium salt INT (2-[4-iodophenyl]-3-[4-nitrophenyl]-5-phenyltetrazolium chloride).
Figure 1:
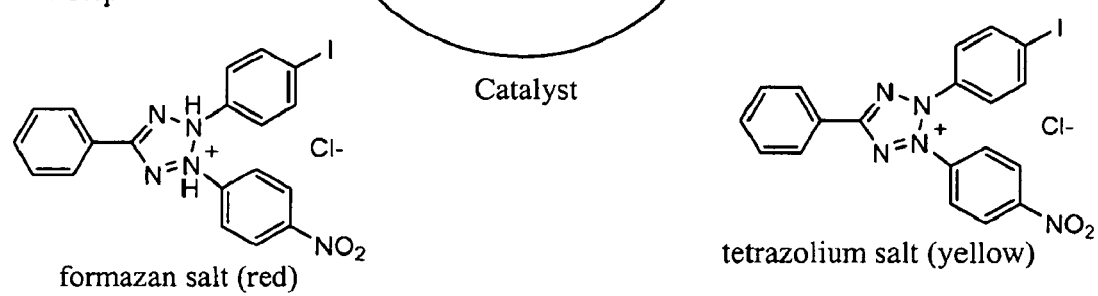
Figure 2:
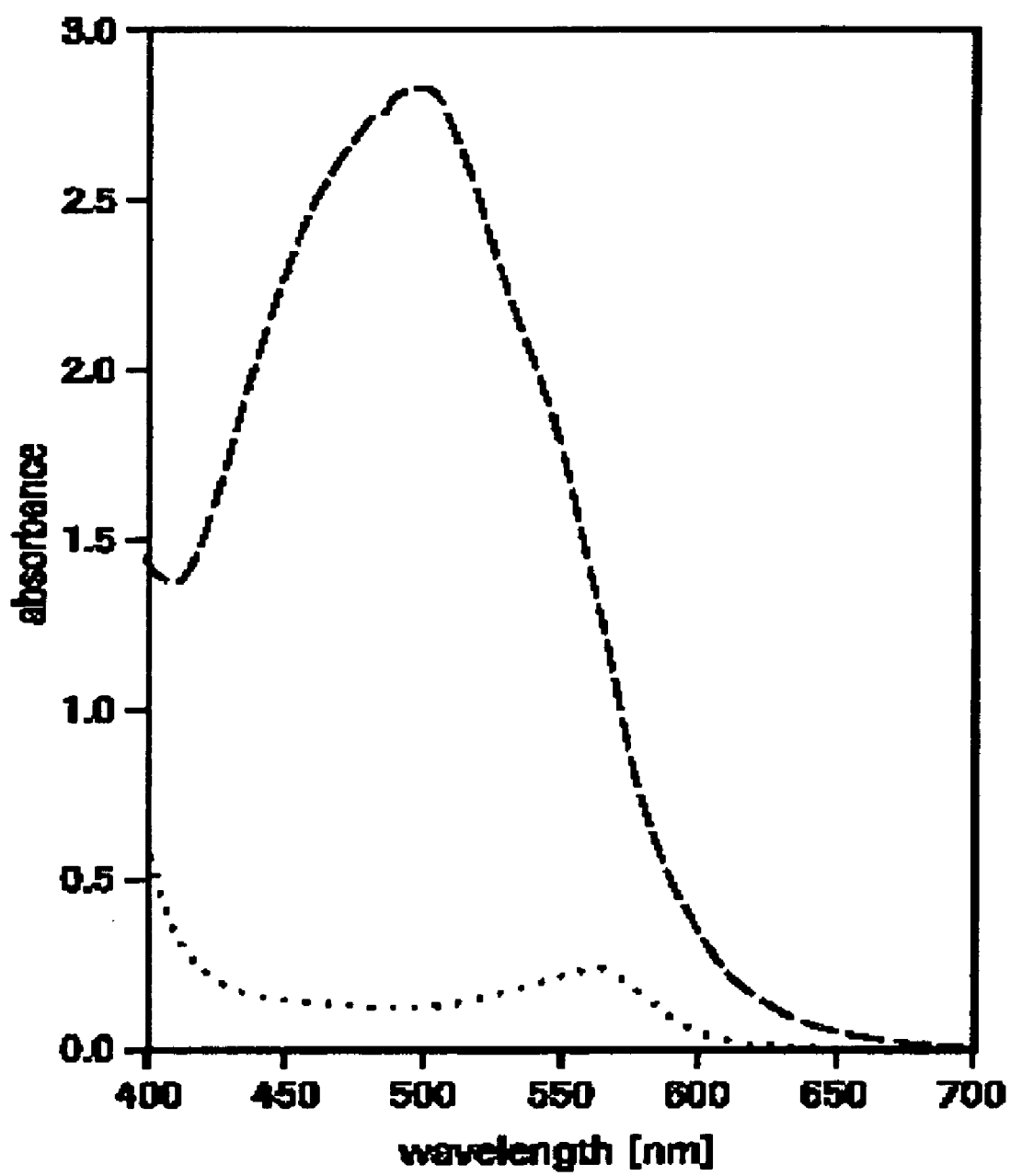
FIG. 2: Absorption spectrum of the working solution from the cytotoxicity detection kit (LDH). The reaction mixture from the cytotoxicity detection kit (LDH) was added to RPMI 1640 medium containing 1% bovine serum albumin (BSA) and the absorption spectrum was measured in the absence ( . . . ) and presence (-) of LDH.

The present invention is based on a method for the calorimetric measurement of enzyme activities in the presence of cells, characterized in that one or more substances are added to cells which minimize the light scattering and absorption caused by the cells.

This is essentially achieved by a method comprising the following steps
  preparing a cell suspension or a cell lysate containing cell components
  adding a chromogenic substrate at the start of the enzyme reaction
  adding a first additional substance to stop the enzyme reaction
  colorimetric measurement
wherein a second additional substance which reduces the light scattering and/or absorption caused by the cells or the cell components is added during or after termination of the enzyme reaction Usually if the cell density is high, a cell-free supernatant has to be firstly formed by centrifugation which, after it has been removed, can then be measured. The invention described here avoids these additional working steps by adding reagents to the cells during or at the end of the test which minimize light scattering and absorption caused by the cells. This can for example be achieved by adjusting the refractive index of the cells to that of the test medium and thus reducing or minimizing the light scattering. This can for example be achieved by adding glycerol or ethylene glycol up to a maximum final concentration of 70%.

In alternative embodiments the volume of the cells and thus their absorption can be reduced by adding substances such as salts at high molar concentrations which remove water from the cells due to the high osmotic pressure of the medium. As a result the volume of the cells decreases which increases the transparency of the sample to be tested. The addition of at least 0.3 M NaCl has for example been proven to be sufficient in this connection.

The light scattering and absorption of cells is preferably reduced by permeabilization of the cell membrane. This can for example be carried out by lytic enzymes such as lipases or mellitin.

Detergents are, however, also preferably suitable for permeabilization. A person skilled in the art knows a large variety of different detergents. A distinction is made between ionic, non-ionic and zwitterionic detergents. Among the ionic detergents a further distinction is made between anionic detergents such as SDS (sodium dodecyl sulphate), N-laurylsarcosine or sodium cholate and cationic detergents such as cetyltrimethylammonium bromide (CTAB) or dodecyltrimethylammonium bromide (DTAB). Examples of non-ionic detergents are known to a person skilled in the art under the names Triton® X-100 (octylphenoxypolyethoxyethanol), Nonidet P40 or TWEEN® 20 (polyoxyethylene(20)sorbitan monolaurate). Common zwitterionic reagents are for example CHAPS ([3-(3-cholamidopropyl)dimethyl-ammonium]-1-propane sulfonic acid) or Zwittergent® 3-12(n-dodecyl-N,N-dimethyl-3-ammonium-1-propanesulfonic acid.

Surprisingly the cationic detergents CTAB and DTAB increased the absorption of the reduced INT substrate which resulted in an increase in the sensitivity of the test. In addition the signals with these detergents were very stable over a period of 5 days whereas the signal decreased considerably with pure PBS buffer or with the non-ionic detergent TritonX100, and the anionic detergent SDS caused a rapid loss in absorption.

All detergents were added at a maximum final concentration of 3% (v/v) and preferably up to 1% (v/v).

If the cell membrane is permeabilized in order to reduce the light scattering and absorption of the cells, care must be taken that substances released by this step do not affect the reaction. Thus for example enzymes could be released which produce additional reaction product or further convert the reaction product so that it is no longer measurable. Thus for some enzymatic reactions it makes sense to stop the reaction at the same time as permeabilizing the cells. Suitable measures for this depend on the reaction which is to be measured.

Suitable measures for terminating enzymatic reactions can for example be the addition of specific enzyme inhibitors or a change in the reaction conditions such that the reaction is terminated. In many cases a change in the pH of the reaction medium is suitable for stopping the reaction. In the cases studied here in the examples NaOH and preferably HCl was used to change the pH. HCl was also suggested as a stop reagent for LDH in the Cytotoxicity Detection Kit (LDH) (Roche Applied Science Cat. No. 11644793001). In their publication Decker and Lohmann-Matthes (Decker, Thomas and Lohmann-Matthes, Marie-Luise, J. Immun. Meth. 15 (1988) 61-69) propose a 15 mM sodium oxamate solution as an inhibitor to stop LDH.

Furthermore, enzymatic reactions can be stopped by adding protein-denaturing substances such as urea or by adding proteases.

If these substances, whose addition minimizes the turbidity of the sample caused by cell components, are already added at the start of the reaction or during the reaction then it is necessary that these substances do not influence the enzyme reaction as such.

The present invention also concerns the use of certain substances for the colorimetric measurement of enzyme activities in the presence of cells or cell components characterized in that these substances reduce light scattering and absorption caused by cells or cell components and in doing so do not affect the enzyme activities.

The proteins described above such as lipases or mellitin have proven to be suitable for such a use.

However, the use of appropriate detergents is particularly preferred such as N-laurylsarcosine, sodium cholate, cetyltrimethylammonium bromide (CTAB), dodecyltrimethylammonium bromide (DTAB), Triton® X-100 (octylphenoxypoly-ethoxyethanol), Nonidet P40, TWEEN® 20 (polyoxyethylene(20)sorbitan monolaurate), CHAPS ([3-(3-cholamidopropyl)dimethylammonium]-1-propanesulfonic acid) and Zwittergent® 3-12 (n-dodecyl-N,N-dimethyl-3-ammonium-1-propanesulfonic acid). All said detergents are used according to the invention up to a maximum final concentration of 3% (v/v) and preferably up to a maximum final concentration of 1% (v/v).

The present invention also concerns reagent kits that enable the method according to the invention to be carried out. Reagent kits in the sense of the invention can for example be composed of one or more substrates of which at least one changes its colour after the enzymatic conversion such that either the substrate or the product of this reaction can be specifically measured at a certain wavelength. These substrates can be a component of the reagent kit either in a common vessel or, if it ensures a higher stability, in different vessels.

Hence the invention also concerns a kit for the colorimetric measurement of enzyme reactions in cell suspensions or cell lysates containing cell components comprising
 a chromogenic substrate
 a first substance to stop the enzyme reaction
 a second substance which, when added, reduces the light scattering and/or absorption caused by the cells or the cell components.

The second additional substance can for example be a substance which adjusts the refractive index of the suspension or of the lysate to that of the cells or cell components.

Alternatively the second additional substance can be a substance which, due to its molar concentration, removes water from the cells or cell components by osmotic pressure.

The second addition substance can preferably be a substance which dissolves the cell membrane. Such substances can for example be various types of detergents such as those that have been described in connection with the method according to the invention. Alternatively the permeabilizing substances can be appropriate proteins or peptides such as lipases or mellitin.

Additional typical components of a reagent kit are solutions which contain buffer substances and salts optimized for the respective enzyme reaction. These solutions are usually added to the enzyme reaction. These solutions can either be offered separately or in mixtures with other components of the reagent kit. Many enzymes require coenzymes which can also be a component of the reagent kit in a separately filled or common formulation with other enzymes.

In many cases an enzyme reaction to be measured is coupled with other chemical or enzymatic reactions. In this process either additional substrate is then generated for the reaction to be measured or the reaction product is converted further. An example of this is to be found in Corey, Michael J., et al., J. Immun. Meth. 207 (1997) 43-51 in which the released glyceraldehyde-3-phosphate dehydrogenase is used to synthesize ATP via a coupled enzyme reaction. The ATP that is formed in this reaction is used in a bioluminescence reaction with luciferin and luciferase to generate a measurable light signal. Hence reagent kits for such coupled reactions expediently contain other enzymes, as well as coenzymes, reaction buffers and substrates. In addition the reagent kit in the sense of the invention contains at least one substance which minimizes light scattering and absorption caused by the cells and in doing so does not affect the enzyme activity. This substance can be present in a separate bottle or for example be a component of a reaction buffer. In cases in which a cytoplasmic enzyme is measured and a permeabilization of the cell membrane is used to minimize light scattering and absorption caused by the cells, the reagent kit advantageously additionally contains a substance which stops the chromogenic reaction. This component can be in a common formulation with another component of the reagent kit such as the substance for permeabilizing the cell membrane or be a separate component of the reagent kit.

The invention is further elucidated by the following examples, publications and figures the protective scope of which results from the patent claims. The described procedures are to be understood as examples which still describe the object of the invention even after modifications.

SPECIFIC EMBODIMENTS

Example 1

Measurement of the Absorption of Cells after Treatment with Different Reagents The human suspension cell line U 937 was cultured in RPMI 1640 medium (Sigma Company) containing 10% foetal calf serum and 2 mM glutamine. The cells were then washed in fresh RPMI medium and adjusted to 25,000, 50,000 and 100,000 cells/100 μl. 100 μl thereof was in each case transferred to a 96-well standard microtitre plate. 50 μl RPMI medium containing the appropriate reagents was added by pipette to each of the cell solutions.

The absorption of each well was measured at a wavelength of 690 nm after 5 min and 75 min incubation.

The following table shows that the absorption of the cells increases with an increasing cell count. In addition it is clear that all reagents lower the absorption compared to the pure medium but the optimal concentrations to be used still have to be determined.

| Reagent | Cell count | Absorption after 5 min | Absorption after 75 min |
| --- | --- | --- | --- |
| Triton X100 final concentration 1% (v/v) | 25 000 cells | 0.001 | 0.001 |
|  | 50 000 cells | 0.004 | 0.004 |
|  | 100 000 cells | 0.008 | 0.008 |
| SDS final concentration 1% (v/v) (state of the art) | 25 000 cells | 0.002 | 0.003 |
|  | 50 000 cells | 0.006 | 0.006 |
|  | 100 000 cells | 0.010 | 0.010 |
| CTAB final concentration 1% (v/v) | 25 000 cells | 0.006 | 0.003 |
|  | 50 000 cells | 0.031 | 0.014 |
|  | 100 000 cells | 0.025 | 0.018 |
| DTAB final concentration 1% (v/v) | 25 000 cells | 0.005 | 0.006 |
|  | 50 000 cells | 0.012 | 0.011 |
|  | 100 000 cells | 0.024 | 0.021 |
| N-laurylsarcosine final concentration 1% (v/v) | 25 000 cells | 0.001 | 0.002 |
|  | 50 000 cells | 0.003 | 0.004 |
|  | 100 000 cells | 0.012 | 0.013 |
| RPMI (negative control) | 25 000 cells | 0.01 | 0.011 |
|  | 50 000 cells | 0.018 | 0.018 |
|  | 100 000 cells | 0.044 | 0.048 |

Example 2

Termination of the LDH Reaction with Various Stop Reagents

For this experiment lysates of U 937 cells were firstly prepared as a source of LDH. For this purpose $6 \times 10^5$ cells were suspended in 1 ml distilled water and treated with ultrasound until all cells were lysed. Subsequently the lysate was centrifuged for 10 min at 200×g and the supernatant free of cell residues was used for further experiments.

Cell free lysates of 5000 cells in each case were used in an LDH test containing components from the Cytotoxicity Detection Kit (LDH) (Roche Applied Science Cat. No. 11644793).

As a digression from the said kit, a solution consisting of 2 mM INT, 90 mM L-lactate, 100 mM Tris, pH 8.5 without detergent was used as the dye solution.

After a reaction time of 5 min, different stop reagents were added to these mixtures and the absorption was monitored at 492 nm (the absorption maximum of reduced INT).

| Stop reagent | Absorption 0 min after adding stop reagent | Absorption 30 min after adding stop reagent | Absorption 120 min after adding stop reagent |
| --- | --- | --- | --- |
| RPMI medium (negative control) | 0.113 | 0.309 | 0.852 |
| SDS final concentration 3% (v/v) (state of the art) | 0.113 | 0.113 | 0.105 |
| 15 mM sodium oxamate | 0.113 | 0.127 | 0.179 |
| 15 mM sodium oxamate + Triton X100 final concentration 1% (v/v) | 0.113 | 0.127 | 0.191 |

The table shows that SDS as well as sodium oxamate stop the LDH reaction. However, the termination with the oxamate concentration used is not 100% successful as is the case for SDS. An optimization of the oxamate concentration would be necessary in this case. The example with the combination of oxamate with Triton X100 shows that this inhibitor is also active in the presence of this detergent. When using SDS a slight decrease in absorption is observed which indicates an instability of the substrate in combination with SDS.

In another experiment HCl and NaOH were used as a stop reagent.

For this purpose cell-free lysates each of 1000 cells were used in an LDH test with the components from the Cytotoxicity Detection Kit (LDH) containing the modified dye solution. After a reaction time of 30 min different stop reagents were added to these mixtures and the absorption was monitored at 492 nm (the absorption maximum of reduced INT).

| Stop reagent | Absorption 0 min after adding stop reagent | Absorption 30 min after adding stop reagent | Absorption 120 min after adding stop reagent |
| --- | --- | --- | --- |
| RPMI medium | 0.280 | 0.448 | 0.962 |
| 0.2 M HCl | 0.275 | 0.271 | 0.261 |
| 0.2 M HCl + Triton X100 final concentration 1% (v/v) | 0.268 | 0.269 | 0.261 |

In this case it is clear that HCl is a suitable stop reagent for the LDH reaction. The combination of HCl with Triton X100 leads in this case to the same result.

The addition of NaOH at a final concentration of 0.2 M results in an immediate precipitation of the dye.

Example 3

Measurement of Different Amounts of Released LDH in the Presence of High Amounts of Cells Cell-free lysates of 50,000, 10,000 and 1000 U 937 cells were incubated at room temperature in volumes of 50 μl in the wells of a standard microtitre plate for 0, 5 and 30 minutes in a LDH test containing 100 μl reaction solution from the Cytotoxicity Detection Kit (LDH) with a modified dye solution. The reaction was terminated after 5 or 30 minutes incubation time with 6.5 μl 25% HCl. Subsequently 50 μl containing 150,000 U 937 cells was added to each of these mixtures and at the same time 50 μl of various detergent solutions was added.

Subsequently measurements were carried out at a wavelength of 492 nm after 10 minutes and after 5 days. The blank values of a control mixture in which the reaction was immediately stopped after 0 minutes were in each case subtracted from the measured values.

| Reagent | Amount of lysate (cell count) | Absorption after 5 min measurement 10 min after terminating the reaction (measurement after 5 days) | Absorption after 30 min measurement 10 min after terminating the reaction (measurement after 5 days) |
| --- | --- | --- | --- |
| PBS (phosphate buffer containing salts) (negative control) | 50 000 cells | 0.048 (0.024) | 0.88 (0.119) |
| | 10 000 cells | 0.000 (0.000) | 0.067 (0.033) |
| | 1 000 cells | 0.000 (0.000) | 0.000 (0.000) |
| | 0 cells | 0.000 (0.000) | 0.000 (0.000) |
| Triton X100 final concentration 1% (v/v) | 50 000 cells | 0.101 (0.093) | 0.338 (0.150) |
| | 10 000 cells | 0.038 (0.035) | 0.078 (0.065) |
| | 1 000 cells | 0.003 (0.001) | 0.006 (0.001) |
| | 0 cells | 0.000 (0.000) | 0.000 (0.000) |
| SDS final concentration 1% (v/v) (state of the art) | 50 000 cells | 0.093 (0.008) | 0.364 (0.021) |
| | 10 000 cells | 0.011 (0.000) | 0.078 (0.000) |
| | 1 000 cells | 0.000 (0.000) | 0.007 (0.000) |
| | 0 cells | 0.000 (0.000) | 0.000 (0.000) |
| CTAB final concentration 1% (v/v) | 50 000 cells | 0.095 (0.085) | 0.72 (0.63) |
| | 10 000 cells | 0.036 (0.021) | 0.084 (0.077) |
| | 1 000 cells | 0.001 (0.002) | 0.010 (0.004) |
| | 0 cells | 0.000 (0.000) | 0.000 (0.000) |

-continued

| Reagent | Amount of lysate (cell count) | Absorption after 5 min measurement 10 min after terminating the reaction (measurement after 5 days) | Absorption after 30 min measurement 10 min after terminating the reaction (measurement after 5 days) |
|---|---|---|---|
| DTAB final concentration 1% (v/v) | 50 000 cells | 0.88 (0.082) | 0.70 (0.99) |
| | 10 000 cells | 0.034 (0.026) | 0.075 (0.069) |
| | 1 000 cells | 0.002 (0.002) | 0.008 (0.005) |
| | 0 cells | 0.000 (0.000) | 0.000 (0.000) |

It can be seen that LDH can already be detected in the lysate of 10,000 cells in the presence of 150,000 whole cells after 5 minutes reaction time by adding the detergents whereas this is not possible when using pure PBS buffer without detergent. After 30 minutes reaction time the LDH from 1000 cells can already be detected in this background in the detergent-treated samples whereas only 10,000 cells are detectable without detergent. This is due to the fact that a higher background absorption caused by the 150,000 cells is present in the samples that were not treated with detergent.

It was surprisingly ascertained that cationic detergents such as CTAB and DTAB kept the measured values for this colour substrate almost stable over 5 days whereas SDS in this case had a destabilizing effect.

What is claimed is:

1. A method for colorimetric measurement of enzyme activity in the presence of cells comprising the steps of:
    providing a suspension of cells or a lysate of cells comprising cell components and an enzyme whose activity is to be measured,
    adding a chromogenic substrate for the enzyme to start an enzyme reaction,
    adding a reagent comprising HCl to stop the enzyme reaction,
    adding a substance which dissolves a membrane of the cells or the cell components, and
    monitoring a change in absorbance over a period of time of the chromogenic substrate, thereby measuring the enzymatic activity, wherein the enzyme is lactate dehydrogenase (LDH).

2. The method according to claim 1 wherein the substance which dissolves a membrane of the cells of the cell components is a cationic detergent.

* * * * *